United States Patent [19]
Watkins et al.

[11] Patent Number: 5,187,107
[45] Date of Patent: Feb. 16, 1993

[54] $B_{12}$ ENZYME IMUNOASSAY AND SAMPLE PRETREATMENT

[75] Inventors: Michael I. Watkins, Hercules; Clifford R. Bartlett, Fairfield; Edward T. Liang, Hercules; John M. Pocekay, Napa; Mark A. Staples, Richmond, all of Calif.

[73] Assignee: Bio-Rad Laboratories, Inc., Hercules, Calif.

[21] Appl. No.: 722,034

[22] Filed: Jun. 27, 1991

[51] Int. Cl.$^5$ ............... G01N 33/567; G01N 1/00
[52] U.S. Cl. ................... 436/505; 436/175; 436/174
[58] Field of Search ............ 436/505, 175, 174

[56] References Cited

U.S. PATENT DOCUMENTS 4,451,571  5/1984  Allen ............................. 436/505
4,950,612  8/1990  Khanna et al. ................. 436/505

FOREIGN PATENT DOCUMENTS

89/21826  12/1989  PCT Int'l Appl. .

OTHER PUBLICATIONS

Stryer (1981) Biochemistry, WH Freemant Co, CA, pp. 308-311.
Clark (1980) Immunology, John Wiley & Sons, NY, p. 4.
Ellman (1959) Arch Biochem Biophys 82:70-77.
Sutler et al (1989) Mol Immunol 26:221-230.
Cleland (1964) Biochem 3(4)480-482.
Gainer et al (1971) Virology 45:91-100.
Tinoco et al (1978) Physical Chemistry Prentice Hall, NJ, pp. 136-138.

*Primary Examiner*—Christine M. Nucker
*Assistant Examiner*—David R. Preston

[57] ABSTRACT

Denaturing agents used to pretreat test samples for immunoassays are neutralized and deactivated by the addition of a treatment agent which is a combination of a buffering agent in acid form and an agent for converting the sulfhydryl groups of the denaturing agents to a non-active form such as disulfides or alkylthio groups. The treatment agent serves this function without having sufficient denaturing activity by itself to interfere with subsequent steps of the assay procedure. Also disclosed is a protocol for a vitamin $B_{12}$ assay which involves a sequential rather than competitive binding of the $B_{12}$ with excess intrinsic factor followed by the binding of excess enzyme-labeled $B_{12}$ to any remaining intrinsic and immobilizing such intrinsic factor on a solid phase. Various problems associated with $B_{12}$ assays are avoided by this technique.

14 Claims, 1 Drawing Sheet

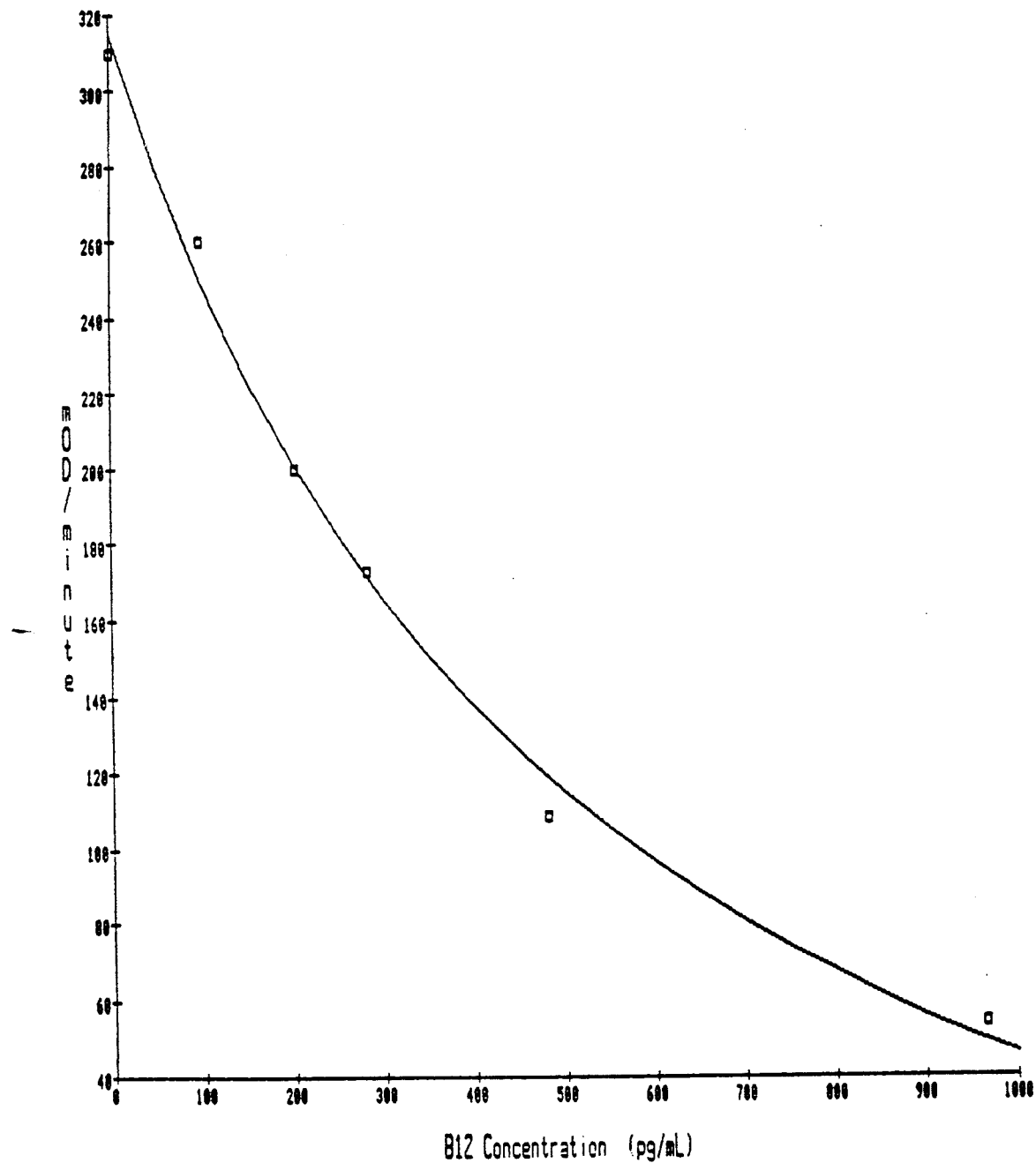

$B_{12}$ ENZYME IMUNOASSAY AND SAMPLE PRETREATMENT

This invention lies in the field of enzyme immunoassays, with a focus in the area of assays for vitamin $B_{12}$.

BACKGROUND OF THE INVENTION

Vitamin $B_{12}$ is an organo-cobalt compound of molecular weight 1355.42. Vitamin $B_{12}$ is not manufactured in the human body and must be ingested in order to meet our nutritional needs. There are several endogenous transport proteins in the body which aid in the absorption of $B_{12}$ from food. Included among these are haptocorrins in the saliva which bind $B_{12}$ as it is released during digestion. Another transport protein is intrinsic factor, found in the intestinal tract, which transport $B_{12}$ across the intestinal mucosa into the blood stream. Further transport proteins are the transcobalamins in the blood stream, which bind $B_{12}$ and deliver it to the tissues of the body that require it. In the blood stream $B_{12}$ is present as hydroxy-, methyl- or adenosylcobalamin. These derivatives are formed by replacing the axial cyano group of $B_{12}$ with the respective functional group. The terms "$B_{12}$" and "vitamin $B_{12}$" as used herein are intended to encompass all of these derivatives collectively.

Since part of the $B_{12}$ in serum is bound to transcobalamin binding proteins, any assay which measures $B_{12}$ must first pretreat the sample to release the $B_{12}$ from these proteins. A further interfering protein is anti-intrinsic factor antibody. This antibody when present, as it is in samples of patients suffering from certain states of pernicious anemia, must also be denatured during pretreatment since such antibody will interfere with any competitive assay which utilizes intrinsic factor as the $B_{12}$-binding protein. A detailed discussion of these problems is found in *Vitamin $B_{12}$*, B. Zagalak and W. Friedrich, editors (Walter de Gruyter & Co., Berlin, 1979); B12 *Volume 1: Chemistry and $B_{12}$ Volume 2: Biochemistry and Medicine*, D. Dolphin, editor (John Wiley & Sons, New York, 1982).

To date the most common assays for Vitamin $B_{12}$ are radioimmunoassays (RIA). Most of these methods utilize intrinsic factor bound to a solid phase and $B_{12}$ radiolabeled with $^{57}Co$ competing with $B_{12}$ in the sample. The sample is pretreated either by a "boil" method or a "no-boil" method. The boil method entails boiling the sample in the presence of a thiol compound at pH 9.3 to denature the $B_{12}$-binding proteins and anti-intrinsic factor antibodies. Potassium cyanide is also included in the pretreatment solution to convert all forms of $B_{12}$ to cyanocobalamin. In the no-boil method, sodium hydroxide and a thiol compound are added to denature the endogenous binding proteins and anti-intrinsic factor antibodies. Potassium cyanide is again added as in the boil method. After pretreatment, a neutralizer is added to bring the pH down to 9.3. This system has been investigated in detail by Allen in U.S. Pat. Nos. 4,188,189, 4,351,822 and U.S. Pat. No. 4,451,571, which note the need to use purified intrinsic factor in a radio dilution assay and cobinamide in addition to alkali and thiol for the no-boil sample pretreatment.

While enzyme immunoassays have been known since the early 1970's—see, for example, Engvall, E., and Perlmann, P., *Immunochem.* 8:871 (1971)—the sensitivity of the method has only recently been sufficiently improved to permit $B_{12}$ to be measured at clinically significant levels (i.e., pg/mL). Such an improvement was first published by Bachas, L. G., Tsalta, C. D., and Meyerhoff, M. E., in *Biotechniques* 4:42-55 (1986), who describe a $B_{12}$ enzyme immunoassay which utilizes intrinsic factor attached to beads, with $B_{12}$-glucose-6-phosphate dehydrogenase as the probe.

Since the Bachas, et. al. publication, several abstracts have appeared relating to $B_{12}$ immunoassays. One of these, Wang, C. -C., Charlton, R. R., "An Enzymometric Assay for Vitamin $B_{12}$ Using Magnetic Particles as Solid Support," *Clin. Chem.* 33:963 (1987), described an assay which uses $B_{12}$ coupled to chromium dioxide, intrinsic factor-$\beta$-galactosidase and $\alpha$-nitrophenyl-$\beta$-D-galactoside as substrate. In May 1989, a poster was presented by Dworschack, et. al. at a CLAS meeting in Los Angeles, pertaining to an assay which employs the CEDIA technology with intrinsic factor as the $B_{12}$-binding protein and $B_{12}$-enzyme donor (enzyme donor is a genetically engineered fragment of $\beta$-galactosidase used in CEDIA assays) as the labeled analyte. Dworschack, R. T., Rosman, D. B., Shindelman, J. E., Lingenfelter, D. S., and Khanna, P. L., "CEDIA $B_{12}$:A Homogeneous Enzyme-Based Ligand Binding Assay for Serum Vitamin $B_{12}$," *15th National Meeting of the Clinical Ligand Assay Society* (Los Angeles; May 1989). Also in 1989, Klukas, et. al. presented a chemiluminescent $B_{12}$ immunoassay, utilizing intrinsic factor bound to magnetic particles and a $B_{12}$-acridinium ester tracer. Klukas, C., Williams, M., Berg, M., Kozel, P., and Hudson, T., "A Chemiluminescence Receptor Assay for Vitamin $B_{12}$," *Clin. Chem.* 35:1194 (1989). In July 1990, Kuemmerle presented another version of a non-isotopic $B_{12}$ EIA at an AACC meeting in San Francisco. The assay employs intrinsic factor bound to a polymeric microspherical solid phase and a $B_{12}$ derivative coupled to a reporter enzyme. Kuemmerle, S. C., Boltinghouse, G. L., Delby, S. M., Lane, T. L., Simondsen, R. P., "IMx Assay for Vitamin $B_{12}$," *Clin. Chem.* 36:969 (1990).

Of further possible interest are an International Patent Application published under the Patent Cooperation Treaty, Oh, C. S., et. al. (Beckman Instruments, Inc.) WO 89/12826, publication date December 28, 1989; and a published European Patent Application, Hoyle, et. al., EP 0378197A2, published Oct. 1, 1990, both for $B_{12}$ non-isotopic assays. The Oh document describes a $B_{12}$ EIA using biotinylated intrinsic factor, avidin-horseradish peroxidase and $B_{12}$ bound to a solid phase. The Hoyle document contains a $B_{12}$ EIA using streptavidin bound to a solid phase, biotinylated monoclonal anti-$B_{12}$ and $B_{12}$-horseradish peroxidase.

Also of possible relevance to this invention is an amplification method, recently reported by Self, C. H., EP 0027036B1, October 1988, which amplifies the signal of the labeling enzyme (alkaline phosphatase) approximately 100-fold.

A further document of possible relevance is an investigation of a solid phase system for ELISA assays where streptavidin is bound to a biotinylated protein which in turn is adsorbed onto a microtiter plate, as reported by Suter, M., Butler, J. E., and Peterman, J. H., in "The Immunochemistry of Sandwich ELISAs-III. The Stoichiometry and Efficacy of the Protein-Avidin-Biotin Capture (PABC) System," *Molecular Immunoo.* 26:221-230 (1989).

Among these methods of the prior art, various difficulties and deficiencies have been noted. The "no-boil" pretreatment method of Allen as referred to above, for example, utilizes treatment reagents which have the potential of denaturing and otherwise detrimentally modifying the various enzymes and binding proteins which might be used in the assay. This will lower the accuracy and reproducibility of the assay. Also, the amplification method of Self referred to above has not been applied to $B_{12}$ assays, since it requires the use of an enzyme-labelled $B_{12}$, which has a much lower binding affinity for proteins than does unlabelled $B_{12}$ This has interfered with the development of competitive binding assays in particular for $B_{12}$. A still further difficulty arises from the fact that the ability of intrinsic factor to bind to $B_{12}$ involves a conformational change in intrinsic factor, and the ability of intrinsic factor to undergo such a change varies with the operating conditions. For maximum binding activity, the intrinsic factor must be in solution. The present invention addresses these and other disadvantages of prior art methods.

SUMMARY OF THE INVENTION

According to one aspect of this invention, the denaturing agents in the no-boil method of vitamin $B_{12}$ pretreatment are retained in the sample mixture after use, and combined with a treatment agent which deactivates the denaturing agents without itself having a denaturing effect on any proteins or enzymes subsequently added to perform the assay. The assay may thus be performed without removing any of the treatment agents from the reaction mixture Since the denaturing agents include an inorganic base and a thiol, the treatment agent includes a buffering agent in acid form to lower the pH of the base, and an agent for converting the sulfhydryl groups of the thiol to a non-active form such as disulfides or alkylthio groups. The sulfhydryl group converting agent may therefore be either an oxidizing agent or an alkylating agent.

Another aspect of this invention resides in a protocol for the assay itself, which permits the use of enzyme-labeled $B_{12}$ without suffering a detriment from the lowered protein binding affinity due to the presence of the enzyme or the use of derivatized $B_{12}$, and which permits the use of intrinsic factor as the binding member with the reaction between $B_{12}$ and intrinsic factor occurring entirely in the liquid phase. This protocol proceeds as follows:

(1) The test sample, once the $B_{12}$ contained in the sample has been freed of all endogenous binding proteins, is reacted with an excess of biotinylated intrinsic factor to form a complex. This reaction occurs entirely in solution in the liquid phase.

(2) Enzyme-labeled vitamin $B_{12}$ is then added and the solution is incubated with solid-phase streptavidin. The result of this incubation is that both the complex formed in step (1) and unreacted biotinylated intrinsic factor become immobilized on the solid phase by a streptavidin-biotin interaction, and the immobilized biotinylated intrinsic factor which had not formed a complex with $B_{12}$ from the test sample binds to enzyme-labeled $B_{12}$. At this stage, immobilized species on the solid phase includes the $B_{12}$ from the sample plus a portion of the enzyme-labeled $B_{12}$, while an amount of enzyme-labeled $B_{12}$ remains in solution. Note that sufficient biotinylated intrinsic factor is used such that most if not all of the sample $B_{12}$ is consumed in step (1), and that the enzyme-labeled $B_{12}$ in step (2) consumes the remaining biotinylated intrinsic factor while displacing substantially none of the sample $B_{12}$ which is already bound.

(3) The solid and liquid phases are then separated, and the level of enzyme activity in either the solid phase or the liquid phase is then determined and related by appropriate calibration curves to the concentration of vitamin $B_{12}$ in the test sample.

Further features and advantages of the invention will become apparent from the descriptions which follow.

BRIEF DESCRIPTION OF THE DRAWING

The FIGURE attached hereto is a plot of a dose-response curve for vitamin $B_{12}$ typical or those obtained using the assay of the present invention.

DETAILED DESCRIPTION OF THE INVENTION AND PREFERRED EMBODIMENTS

The buffering agent in the treatment mixture used after denaturation of the test sample may be any buffer which can be applied in acid form to lower the pH to an acceptable level for the assay, and which will then maintain the pH at or close to that level during the succeeding assay reactions. Examples of such buffers are phosphate buffers, borate buffers, acetate buffers, succinate buffers and tris(hydroxymethyl)-aminomethane. Phosphate buffers, particularly sodium or potassium phosphate monobasic, are preferred. The buffer will be selected and adjusted as and if necessary to provide the treated test sample with a pH falling within the range of from about 6.5 to about 8.0, preferably from about 7.0 to about 7.4. Amounts and methods of adjusting the pH are well known among those skilled in the art.

Oxidizing agents for deactivating the sulfhydryl group of the thiol will be any such agents which have an oxidizing potential and reaction rate sufficiently high to achieve oxidation of the sulfhydryl groups, yet insufficient to cause by themselves any substantial denaturation of proteins and enzymes such as those to be added in subsequent steps in the assay procedure. Examples of such oxidizing agents are iodate salts, nitrite salts, bromate salts, dithionate salts, and Ellman's reagent (5,5'-dithiobis (2-nitrobenzoic acid). Iodate salts, particularly sodium and potassium iodate, are preferred.

Alkylating agents for deactivating the sulfhydryl group of the thiol will be any such agents capable of converting the sulfhydryl groups to alkylthio groups under the conditions prevailing in the test sample following the denaturing pretreatment. Examples of such agents are iodoacetic acid, methyl maleimide, 2-bromoethylamine, and N-iodosuccinimide.

Optimal concentrations of the buffer and the oxidizing or alkylating agent for use in any particular treatment procedure in accordance with this invention are well within the skill of the experienced technician and readily determinable by routine experimentation.

The pretreatment materials for the no-boil method of protein denaturation, whose administration precedes the administration of the combination of buffer and sulfhydryl deactivating agent, may be constituted and applied according to known methods, in accordance with the Allen patents referenced above, the disclosures of which are incorporated herein by reference. Typical pretreatment solutions contain an inorganic base such as sodium or potassium hydroxide, and a thiol such as dithiothreitol, $\beta$-mercaptoethanol, thioglycolate, thioglycerol or 3-mercaptopropionic acid. The most commonly used are sodium hydroxide and dithiothreitol. Typical pretreatment solutions further contain potassium cyanide to convert all forms of cobalamin to cyanocobalamin, as well as cobinamide, a $B_{12}$ analog, in the form of dicyanocobinamide, which serves to saturate all R-binder proteins present in the sample, preventing them from renaturing in this and subsequent steps. The inorganic base and the thiol are generally stored as individual solutions, one containing the base plus potassium cyanide and dicyanocobinamide, and the other containing the thiol and sodium chloride.

While the pretreatment, neutralization and deactivation procedures are described herein primarily in connection with assays for vitamin $B_{12}$, they are applicable in a similar manner to assays for a wide range of species which tend to bind to endogenous proteins when present in a biological sample. In this aspect of the invention, the species to be detected by the assay is not critical to the invention.

For application of the present invention to assays for vitamin $B_{12}$, such assays may be performed on any biological fluid sample suspected of containing vitamin $B_{12}$ and for which the vitamin $B_{12}$ content is sought to be determined. Such assays is typically performed on human plasma or serum.

A wide variety of enzymes may be used for the enzyme-labeled vitamin $B_{12}$, including any enzyme which can serve as a label in a detection method. Many such enzymes and substrates for their detection are known among those skilled in the art of immunoassays. A preferred enzyme is alkaline phosphatase, and a preferred detection method is the enzyme amplification method of Self, referenced above and incorporated herein by reference.

A typical method involving alkaline phosphatase uses $\beta$-nicotinamide adenine dinucleotide phosphate, reduced form ($\beta$-NADPH) as the substrate. The alkaline phosphatase cleaves the phosphate group to form $\beta$-nicotinamide adenine dinucleotide, reduced form ($\beta$-NADH). This is followed by addition of a color development reagent composed of diaphorase, iodonitrotetrazolium violet (INT), ethanol and alcohol dehydrogenase. Only the cleaved product, $\beta$-NADH, formed during the substrate incubation step can initiate the amplification cycle. The $\beta$-NADH is oxidized to $\beta$-NAD by diaphorase with concomitant reduction of INT to a colored product (measurable at 490nm). To complete the cycle alcohol dehydrogenase simultaneously reduces $\beta$-NAD to $\beta$-NADH and oxidizes ethanol to acetaldehyde. The cycle then begins again, and the speed at which the color is generated is dependent upon the amount of $\beta$-NADH originally present.

As stated above, this detection procedure may be performed on either the solid phase or the liquid phase. For solid phase procedures, the solid phase is placed in contact with liquid solutions of the substrate and other detection agents, and color changes observed and quantified in those solutions. For liquid phase procedures, the liquid phase is combined with liquid solutions of the substrate and other detection agents, and color changes observed and quantified in a similar manner.

The solid phase may be of any configuration which is suitable and appropriate for the procedures involved in the assay. Examples are beads, test tubes and microtiter plates.

The formation of the other reagents utilized in the assay is achieved by conventional means reported in the literature To form an alkaline phosphatase-labeled $B_{12}$, for example, acid hydrolysis is performed on the propionamide groups on the corrin ring of $B_{12}$. This is followed by reacting $B_{12}$ monocarboxylic acid with N-hydroxysuccinimide (NHS) in the presence of dicyclohexylcarbodiimide in an anhydrous, aprotic solvent system. This results in the formation of an NHS ester of $B_{12}$ monocarboxylic acid which is then allowed to react with the amine groups of alkaline phosphatase in aqueous media.

Biotinylated intrinsic factor is likewise prepared by known procedures, one such method involving the use of sulfosuccinimidyl 6-(biotinamido) hexanoate as the biotinylating agent. The concentration of biotinylated intrinsic factor used in the assay may be adjusted to give a dose response curve which has the greatest sensitivity in the diagnostic range expected for the assay. Such an adjustment is well within the skill of the experienced immunoassay technician, and readily determinable by routine experimentation. Intrinsic factor is specific for $B_{12}$ and does not cross-react with cobinamide or other $B_{12}$ analogs.

Immobilization of streptavidin on a solid phase such as a microtiter plate is conveniently achieved by adsorbing a biotinylated carrier protein onto a microtiter plate and then allowing streptavidin to bind to the biotin-protein plate.

An assay kit including all components necessary for the assay will typically include the following:

| 1. Standards | |
|---|---|
| Cyanocobalamin | pg/mL range |
| Human Serum Albumin | 7% |
| Sodium Chloride | 0.9% |
| Sodium Azide | 0.1% |
| 2. Enzyme Conjugate Solution | |
| $B_{12}$-Alkaline Phosphatase Conjugate | |
| Triethanolamine hydrochloride | 10 mM |
| Sodium Azide | 0.1% |
| Sodium chloride | 0.85% |
| Magnesium Chloride | 1 mM |
| Zinc Sulfate Heptahydrate | 0.1 mM |
| Human Serum Albumin | 1% |
| Polyethyleneglycol 8000 | 5% |
| Tween 20 | 0.05% |
| 3. Binding Protein Conjugate Solution | |
| Biotin-Intrinsic Factor Conjugate | |
| Triethanolamine hydrochloride | 10 mM |
| Sodium Azide | 0.1% |
| Sodium chloride | 0.85% |
| Magnesium Chloride | 1 mM |
| Zinc Sulfate Heptahydrate | 0.1 mM |
| Human Serum Albumin | 1% |
| Polyethyleneglycol 8000 | 5% |
| Tween 20 | 0.05% |
| 4. Neutralizer | |
| Potassium Iodate | 100 mM |
| Potassium Phosphate Monobasic Monohydrate | 260 mM |
| 5. Pretreatment Solution, Part A | |
| Sodium Hydroxide | 1 M |
| Potassium Cyanide | 100 µg/mL |
| Dicyanocobinamide | 1 µg/mL |
| 6. Pretreatment Solution, Part B | |
| Dithiothreitol | 20 mg/mL |
| Sodium Chloride | 10 mM |
| 7. Wash Buffer, pH 7.4 | |
| Triethanolamine Hydrochloride | 10 mM |
| Sodium Chloride | 0.88% |
| Tween 20 | 0.05% |
| Kathon CG | 0.06% |
| 8. Pretreatment Microtiter Plates | |
| Blank polystyrene microtiter plates | |
| 9. Assay Microtiter Plates | |
| Polystyrene microtiter plates coated with biotin-bovine serum albumin to which streptavidin is attached | |
| 10. Lyophilized Substrate | |
| $\beta$-Nicotinamide Adenine Dinucleotide Phosphate | |

| -continued | |
|---|---|
| (reduced form) | |
| 11. Substrate Diluent, pH 9.5 | |
| Diethanolamine | 50 mM |
| Ethanol | 4% |
| Magnesium Chloride | 1 mM |
| Sodium Azide | 0.02% |
| Tween 20 | 0.1% |
| 12. Lyophilized Amplifier | |
| Alcohol Dehydrogenase | |
| Diaphorase | |
| 13. Amplifier Diluent | |
| Sodium Phosphate Monobasic Monohydrate | 1 mM |
| Sodium Azide | 0.02% |
| Ethylene Glycol | 8% (volume basis) |
| Iodonitrotetrazolium Violet | 2 mM |

The following examples are offered by way of illustration, and are intended neither to limit nor to define the invention in any manner.

EXAMPLE 1

Biotinylation of Intrinsic Factor

A reaction flask was charged with 200μL of 0.5 mg/mL intrinsic factor, 166μL of deionized water and 50μL of 1M sodium bicarbonate. Separately, a solution was formed by dissolving 5 mg of sulfosuccinimidyl 6-(biotinamido)-hexanoate in 1 mL of deionized water. Immediately after formation of the latter, a portion (56μL) of the biotin solution was added to the intrinsic factor solution with stirring. The resulting reaction mixture was allowed to react at 4° C. for 16 hours.

After this time, a 100μL quantity of a solution containing 1% human serum albumin, 10 mM trishydroxymethylaminomethane, 0.85% sodium chloride, and 0.1% sodium azide (10 mM TBS/azide), at pH 7.4 was added. The resulting solution was washed six times using a Centricon 30 microconcentrator and 10 mM TBS/azide. The wash buffer contained 10 mM triethanolamine, 0.88% sodium chloride, 0.05% Tween 20 and 0.06% Kathon CG, pH 7.4. After washing, the solution volume was increased to 1 mL and an equal volume of conjugate diluent was added. The conjugate diluent contained 10 mM triethanolamine, 0.1% sodium azide, 0.85% sodium chloride, 1mM magnesium chloride, 0.1 mM zinc sulfate heptahydrate, 1% human serum albumin, 5% polyethylene glycol and 0.05% Tween 20, pH 7.4.

EXAMPLE 2

Coupling of $B_{12}$ to Alkaline Phosphatase

Before $B_{12}$ can be coupled to alkaline phosphatase it must first be derivatized by acid hydrolysis of the propionamide groups of the corrin ring. This was achieved by first adding 600 mg of $B_{12}$ to 12mL of 0.1 M hydrochloric acid. The solution was stirred in the dark at ambient temperature for 72 hours. After this time, the pH was adjusted to 4.0 with 1 M sodium hydroxide.

The reaction mixture was then applied to an alumina column, which was then eluted with water. Unhydrolyzed material passed through the column while the mono-, di- and tri-carboxylic acids were retained. The monocarboxylic acid was eluted off with 0.1 M ammonium hydroxide. The fractions containing the desired mixture of b, d and e isomers of $B_{12}$-monocarboxylic acid were pooled, concentrated and acidified to pH 4.0. The product was then extracted into 90% phenol. Ether was added to the phenol extracts. The phenol/ether layer was then extracted with deionized water, with the product residing in the aqueous layer. The combined aqueous extract was washed with ether. The final aqueous layer was lyophilized to give 65 mg of a mixture of the b, d and e isomers of the monocarboxylic acid of $B_{12}$.

The N-hydroxysuccinimide active ester of $B_{12}$ was then formed and reacted with alkaline phosphatase. To accomplish this, $B_{12}$ monocarboxylic acid (20 mg), N-hydroxysuccinimide (22 mg) and 1,3 dicyclohexylcarbodiimide (40 mg) were dissolved in anhydrous N,N-dimethylformamide (700μL). The resulting solution was stirred in the dark at 4° C. for 16 hours. The solution was then centrifuged and the pellet discarded.

To 1.27 mg of calf intestine alkaline phosphatase, in 5.86mL of 0.1 M phosphate buffer, 0.1 M sodium chloride, pH 7.4, was added 140μL (4.69 mg) of the supernatant of the solution containing the $B_{12}$ active ester. The mixture was stirred for 16 hours in the dark at 4° C. After this time the reaction mixture was dialyzed against 50 mM Tris, 0.1% sodium azide, 0.1 M sodium chloride, 1 mM magnesium chloride and 0.1 mM zinc chloride, pH 7.6, 0.1% Norit A (charcoal). The conjugate was purified by HPLC using a size exclusion column.

EXAMPLE 3

Preparation of Streptavidin-Coated Microtiter Plates

The preparation of streptavidin-coated microtiter plates requires biotinylated carrier protein. For this example the carrier protein was bovine serum albumin (BSA). A solution was prepared by dissolving 100 mg of BSA in a mixture of 10mL of 1M sodium bicarbonate and 9 mL of deionized water. A biotin solution was then prepared by dissolving 79.5 mg of sulfosuccinimidyl 6-(biotinamido) hexanoate 1 mL of deionized water. Immediately after it was formed, the biotin solution was added to the BSA solution with stirring. The resulting solution was allowed to stand for 16 hours at 4° C., then washed using a Centricon 30 microconcentrator and 10 mM phosphate-buffered saline (PBS), 0.1% sodium azide, pH 7.4.

The biotin-BSA solution was diluted to 2.5 μg/ml using 10 mM PBS, pH 7.4. The wells of a microtiter plate were then charged with 100μL/well of this solution, and the plate was incubated overnight at room temperature. The next day the plate was washed with wash buffer. Streptavidin was dissolved in a solution of 1% BSA, 10 mM PBS to give a final concentration of 4μg/mL. This was followed by the addition of this solution to the wells of the microtiter plate at 10 was then incubated overnight at room temperature. The next day the plate was washed with wash buffer, and 5% sucrose in 10 mM PBS at 100μL/well, pH 7.4, was added. The plate was then incubated overnight at room temperature. The next day the solution was decanted and the plate blotted dry. The plate was stored in a plastic bag with desiccant at 4° C.

EXAMPLE 4

$B_{12}$ Assay Protocol and Results

Into each well of an uncoated microtiter plate was placed 30μL of standard, control or sample, followed by 60μL of a 1:1 mixture of pretreatment solution A and pretreatment solution B. These pretreatment solutions were as follows:

Pretreatment solution A: 1M sodium hydroxide, 100 μg/mL potassium cyanide and 1 μg/mL dicyanocobinamide Pretreatment solution B: 20 mg/mL dithiothreitor and 10 mM sodium chloride The plate was then shaken briefly, covered and placed in a 37° C. incubator for 20 minutes. Neutralizer solution (150 μL), consisting of 100 mM potassium iodate and 260 mM potassium phosphate monobasic, was then added, followed by 30 μL of binding protein. The plate was then shaken briefly again, covered and placed in a 37° C. incubator for 30 minutes.

Into each well of a streptavidin/biotin-BSA coated microtiter plate was placed 35μL of the enzyme conjugate using a multichannel pipette, followed by 70μL of the pretreated standard, control or sample. The plate was then shaken briefly, covered and placed in a 37° C. incubator for 30 minutes. The plate was then washed and blotted dry, and substrate solution (100μL/well) was added. The plate was again shaken briefly, covered and placed in a 37° C. incubator for 30 minutes. Finally, 100μL of amplifier solution was added to each well. The rate of change in optical density at 490 nm was then read on a microtiter plate reader.

The figure attached hereto is a plot of the dose-response curve obtained using this protocol. The vertical axis represents the rate of color development in milli-optical density units per minute, whereas the horizontal axis represents the $B_{12}$ concentration in picograms per milliliter.

The foregoing is offered primarily for purposes of illustration. It will be readily apparent to those skilled in the art that the operating conditions, materials, procedural steps and other parameters of the assay described herein may be further modified or substituted in various ways without departing from the spirit and scope of the invention.

What is claimed is:

1. A process for preparing a test sample for an enzyme immunoassay in which the presence therein of vitamin $B_{12}$ will be detected, wherein at least a portion of said vitamin $B_{12}$ if present in said test sample is bound to endogenous binding proteins capable of interfering with said enzyme immunoassay, said processing comprising:
   (a) combining said test sample with an inorganic base and a thiol to form a first mixture;
   (b) incubating said first mixture to cause said inorganic base and said thiol to denature substantially any of said endogenous binding proteins present in said test sample and to thereby release substantially any of said vitamin $B_{12}$ present in said test sample from said engogenous binding proteins, thereby forming a second mixture; and
   (c) combining said second mixture with
      (i) a buffering agent in acid form, and
      (ii) a sulfhydryl group converting agent selected from the group consisting of (1) oxidizing agents having an electrochemical potential of a level selected to oxidize any sulfhydryl compounds present in said first mixture to disulfides yet to substantially avoid denaturation of further proteins not already denatured, and (2) alkylating agents, to lower the pH of said second mixture to a value within the range of approximately 6.5 to approximately 8.0 and to convert any thiol groups remaining therein to disulfide or alkylthio groups.

2. A process in accordance with claim 1 in which step (c) comprises lowering said pH to a value within the range of approximately 7.0 to approximately 7.4.

3. A process in accordance with claim 1 in which said buffering agent is a member selected from the group consisting of a phosphate buffer, borate buffer, acetate buffer, succinate buffer, and tris(hydroxymethyl)aminomethane.

4. A process in accordance with claim 1 in which said buffering agent is a dihydrogen phosphate buffer.

5. A process in accordance with claim 1 in which said sulfhydryl group converting agent is an oxidizing agent selected from the group consisting of an iodate salt, nitrite salt, bromate salt, dithionate salt, and 5,5'-dithiobis (2-nitrobenzoic acid).

6. A process in accordance with claim 1 in which said sulfhydryl group converting agent is an iodate salt.

7. A process in accordance with claim 1 in which said inorganic base is a member selected from the group consisting of sodium hydroxide and potassium hydroxide, and said thiol is a member selected from the group consisting of dithiothreitol, β-mercaptoethanol, thioglycolate, thioglycerol, and 3-mercaptopropionic acid.

8. A process in accordance with claim 1 in which said inorganic base is sodium hydroxide, and said thiol is dithiothreitol.

9. A process in accordance with claim 1 in which said inorganic base is sodium hydroxide, said thiol is dithiothreitol, said buffering agent is a dihydrogen phosphate buffer and said sulfhydryl group converting agent is an iodate salt.

10. A process for determining the amount of vitamin $B_{12}$ in a test sample containing vitamin $B_{12}$ within a predetermined range of concentration, said process comprising:
   (a)
      (i) combining said test sample with an inorganic base and a thiol and incubating the resulting mixture to cause said inorganic base and said thiol to denature any endogenous binding proteins present in said test sample and to thereby release therefrom all vitamin $B_{12}$ bound thereto; and
      (ii) combining the mixture resulting from step (a) (i) with
         (1) a buffering agent in acid form, and
         (2) a sulfhydryl group converting agent selected from the group consisting of (a) oxidizing agents having an electrochemical potential of a level selected to oxidize any sulfhydryl compounds present in said first mixture to disulfides yet to substantially avoid denaturation of further proteins not already denatured, and (b alkylating agents,
      to lower the pH of said second mixture to a value within the range of approximately 6.5 to approximately 8.0 and to convert any thiol groups remaining therein to disulfide groups;
   (b) combining said test sample with biotinylated intrinsic factor in a first solution, said biotinylated intrinsic factor being in excess of the maximum of said predetermined range, and incubating said first solution to cause substantially all vitamin $B_{12}$ therein to combine with biotinylated intrinsic factor to form a complex;
   (c) combining said first solution with enzyme-labeled vitamin $B_{12}$ in a second solution in the presence of streptavidin immobilized on a solid phase, said enzyme-labeled vitamin $B_{12}$ and said streptavidin each being in excess of said biotinylated intrinsic factor of step (b), and incubating said second solution and said streptavidin to cause said complex and biotinylated intrinsic factor free of vitamin $B_{12}$ in said second solution to become bound to said streptavidin and to cause said biotinylated intrinsic factor free of vitamin $B_{12}$ in said second solution to become complexed to said enzyme-labeled vitamin $B_{12}$;

(d) separating said solid phase from said second solution; and (e) determining the level of enzyme activity of either said solid phase or said second solution.

11. A process according to claim 10 in which said test sample is in liquid form, and said biotinylated intrinsic factor of step (b) is in the form of an aqueous solution before being combined with said test sample.

12. A process according to claim 10 in which said test sample is in liquid form, and said enzyme-labeled vitamin $B_{12}$ of step (c) is in the form of an aqueous solution before being combined with said first solution.

13. A process according to claim 10 in which step (b) and (c) are performed at pH's of from about 7.0 to about 8.0.

14. A process according to claim 10 in which the enzyme of said enzyme-labeled vitamin $B_{12}$ is alkaline phosphatase.

* * * * *